(12) United States Patent
Doshi et al.

(10) Patent No.: US 6,443,944 B1
(45) Date of Patent: Sep. 3, 2002

(54) SURGICAL DEVICES COMPRISING ARTICULATED MEMBERS AND METHODS FOR USING THE SAME

(76) Inventors: Rajiv Doshi, 2166 Ash St., Palo Alto, CA (US) 94306; Ryan Abbott, 20661 Forge Way, Apt. 161, Cupertino, CA (US) 95014; Mark Harasym, 598 Hill Rd., Boxborough, MA (US) 01719; Jamie Juliana van Hoften, 1014 Regio Ct., Lafayette, CA (US) 94549

( * ) Notice: Subject to any disclaimer, the term of this patent is extended or adjusted under 35 U.S.C. 154(b) by 0 days.

(21) Appl. No.: 09/574,446

(22) Filed: May 19, 2000

(51) Int. Cl.$^7$ .............................................. A61B 17/00
(52) U.S. Cl. ........................... 606/1; 606/208; 600/143; 901/39
(58) Field of Search ........................... 606/1, 167, 208, 606/50, 51, 52, 46, 205, 206, 207; 74/490.05, 490.06; 901/15, 28, 29, 39; 600/139, 140, 141, 142, 143

(56) References Cited

U.S. PATENT DOCUMENTS

| | | | |
|---|---|---|---|
| 3,799,151 A | * 3/1974 | Fukaumi et al. ................ 128/6 |
| 4,245,624 A | * 1/1981 | Komiya ....................... 600/106 |
| 4,246,661 A | * 1/1981 | Pinson ........................... 3/1.1 |
| 4,432,349 A | * 2/1984 | Oshiro ......................... 600/141 |
| 4,580,551 A | * 4/1986 | Siegmund et al. ........... 600/139 |
| 4,653,476 A | * 3/1987 | Bonnet ....................... 600/106 |
| 5,383,895 A | 1/1995 | Holmes et al. |
| 5,405,344 A | * 4/1995 | Williamson et al. ........ 340/7.29 |
| 5,417,684 A | 5/1995 | Jackson et al. |
| 5,447,403 A | * 9/1995 | Engler, Jr. ..................... 414/4 |
| 5,454,827 A | * 10/1995 | Aust et al. .................. 600/564 |
| 5,474,057 A | * 12/1995 | Makower et al. ........... 600/205 |
| 5,549,636 A | 8/1996 | Li |
| 5,549,637 A | * 8/1996 | Crainich ..................... 606/170 |
| 5,613,973 A | 3/1997 | Jackson et al. |
| 5,645,520 A | * 7/1997 | Nakamura et al. .......... 600/143 |
| 5,713,919 A | 2/1998 | Lahr |
| 5,716,352 A | * 2/1998 | Viola et al. ................... 606/1 |
| 5,718,703 A | * 2/1998 | Chin ........................... 606/46 |
| 5,728,121 A | 3/1998 | Bimbo et al. |
| 5,752,973 A | * 5/1998 | Kieturakis ................. 606/207 |
| 5,772,578 A | * 6/1998 | Heimberger et al. ........ 600/139 |
| 5,776,126 A | * 7/1998 | Wilk et al. ..................... 606/1 |
| 5,797,959 A | 8/1998 | Castro et al. |
| 5,807,376 A | * 9/1998 | Viola et al. ................... 606/1 |
| 5,820,009 A | 10/1998 | Melling et al. |
| 5,868,740 A | * 2/1999 | LeVeen et al. ............... 257/192 |
| 5,891,162 A | 4/1999 | Sugarbaker et al. |
| 5,976,122 A | 11/1999 | Madhani et al. |
| 5,993,447 A | * 11/1999 | Blewett et al. ............. 600/105 |
| 5,997,567 A | 12/1999 | Cangelosi |
| 6,050,992 A | * 4/2000 | Nichols ........................ 606/41 |
| 6,238,414 B1 | * 5/2001 | Griffiths ...................... 606/205 |

OTHER PUBLICATIONS

Doshi et al. (1998). "The design and development of a gloveless endoskeletal prosthetic hand" *J. of Rehabilitation Research and Development*, vol. 35(4): 388–395.

* cited by examiner

*Primary Examiner*—Linda C. M. Dvorak
*Assistant Examiner*—Jocelyn Ram
(74) *Attorney, Agent, or Firm*—Bret E. Field; Bozicevic, Field & Francis (57) ABSTRACT

Surgical devices and methods for their use in manipulating internal body objects are provided. The subject devices have proximal and distal ends separated by an elongate member. Located at the distal end is at least one articulated member, and usually two or more articulated members. A manual means for actuating the one or more distal articulated members is located at the proximal end of the device. The elongate member may be flexible or rigid. The subject devices find use in a variety of applications, and are particularly suited for use in applications in which it is desired to manipulate an internal body object from a location external to the body.

25 Claims, 10 Drawing Sheets

SURGICAL DEVICES COMPRISING ARTICULATED MEMBERS AND METHODS FOR USING THE SAME

FIELD OF THE INVENTION

The field of this invention is medical devices, and more particularly minimally invasive surgical devices.

BACKGROUND OF THE INVENTION

Minimally invasive medical techniques are aimed at reducing the amount of extraneous tissue which is damaged during diagnostic or surgical procedures, thereby reducing patient recovery time, discomfort, and deleterious side effects. Of the large total number of surgeries performed in the United States each year, it is estimated that significant proportion of these surgeries can potentially be performed in a minimally invasive manner. However, only a fraction of this potential number currently use these techniques due to limitations in minimally invasive surgical instruments and techniques and the additional surgical training required to master them.

Advances in minimally invasive surgical technology could have a dramatic impact. The average length of a hospital stay for a standard surgery is 8 days, while the average length for the equivalent minimally invasive surgery is 4 days. Thus, the complete adoption of minimally invasive techniques could save 28,000,000 hospital days, and billions of dollars annually in hospital residency costs alone. Patient recovery times, patient discomfort, surgical side effects, and time away from work are also reduced with minimally invasive surgery.

The most common form of minimally invasive surgery is endoscopy. Probably the most common form of endoscopy is laparoscopy which is minimally-invasive inspection and surgery inside the abdominal cavity. In standard laparoscopic surgery, a patient's abdomen is insufflated with gas, and cannula sleeves are passed through small (approximately ½ inch) incisions to provide entry ports for laparoscopic surgical instruments.

The laparoscopic surgical instruments generally include a laparoscope for viewing the surgical field, and working tools such as clamps, graspers, scissors, staplers, and needle holders. The working tools are similar to those used in conventional (open) surgery, except that the working end of each tool is separated from its handle by an approximately 12 to 15-inch long extension tube.

To perform surgical procedures, the surgeon passes instruments through the cannula and manipulates them inside the abdomen by sliding them in and out through the cannula, rotating them in the cannula, levering (i.e., pivoting) the instruments in the abdominal wall and actuating end effectors on the distal end of the instruments. The instruments pivot around centers of rotation approximately defined by the incisions in the muscles of the abdominal wall. The surgeon monitors the procedure by means of a television monitor which displays the abdominal worksite image provided by the laparoscopic camera.

Similar endoscopic techniques are employed in arthroscopy, retroperitoneoscopy, pelviscopy, nephroscopy, cystoscopy, cisternoscopy, sinoscopy, hysteroscopy and urethroscopy.

The common feature of all of these minimally invasive surgical techniques is that they visualize a worksite within the human body and pass specially designed surgical instruments through natural orifices or small incisions to the worksite to manipulate human tissues and organs thus avoiding the collateral trauma caused to surrounding tissues which would result from creating open surgical access.

There are many disadvantages to current minimally invasive surgical technology. For example, existing MIS instruments deny the surgeon the flexibility of tool placement found in open surgery. Most laparoscopic tools have rigid shafts and are constrained to approach the worksite from the direction of the small incision. Additionally, the length and construction of many endoscopic instruments reduce the surgeon's ability to feel forces exerted by tissues and organs on the end effector of the tool. The lack of dexterity and sensitivity provided by endoscopic tools is a major impediment to the expansion of minimally invasive surgery.

As such, there is much interest in the development of new surgical tools for use in minimally invasive procedures that address one or more of the above disadvantages.

RELEVANT LITERATURE

U.S. Patents of interest include: U.S. Pat. Nos. 5,997,567; 5,976,122; 5,891,162; 5,820,009; 5,797,959; 5,728,121; 5,713,919; 5,613,973; 5,549,636; 5,417,684; and 5,383,895. See also Doshi et al., J. Rehabil. Res. Dev. (1998) 35:388–395.

SUMMARY OF THE INVENTION

Surgical devices and methods for their use in manipulating internal body objects are provided. The subject devices are elongated devices having an elongate member with proximal and distal ends. Located at the distal end is at least one articulated member, and usually two or more articulated members. A manual means for actuating the one or more distal articulated members is located at the proximal end of the device. The elongate members may be flexible or rigid, and both embodiments are encompassed by the subject invention. The subject devices find use in a variety of applications, and are particularly suited for use in applications in which it is desired to manipulate an internal body object from a location external to the body.

DESCRIPTION OF THE SPECIFIC EMBODIMENTS

Surgical devices and methods for their use in manipulating internal body objects are provided. The subject devices have proximal and distal ends separated by an elongate member. Located at the distal end is at least one articulated member, and usually two or more articulated members. A manual means for actuating the one or more distal articulated members is located at the proximal end of the device. The elongate member separating the proximal and distal ends may be rigid or flexible. The subject devices find use in a variety of applications, and are particularly suited for use in applications in which it is desired to manipulate an internal body object from a location external to the body. In further describing the subject invention, the subject devices will be described first both in general terms and in terms of representative embodiments depicted in the figures, followed by a review of representative applications in which the subject devices find use and kits that include the subject devices.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

DEVICES

As summarized above, the subject devices are devices for use in manipulating internal body objects. As such, the subject devices are devices for use in moving an object inside of a body of an animal. A feature of the subject devices is that they are actuatable by an actuation means that is located outside of the body of the animal during use. In other words, the actuation means of the subject devices is separated from the object moving means by a distance which provides for the object moving means to be inside of the animal body and the actuation means to be outside of the body during use.

As such, the subject devices are elongate structures that have a distal end and a proximal end separated by a length of sufficient distance to provide for the above features during use. The proximal end is defined as the end of the device that is not inside the animal body during use, i.e. the end that is most distant or furthest away from the end of the device that is inside of the body during use. In other words, the proximal end of the device is the end of the device that is outside of the body during use. In contrast, the distal end of the device is the end of the device that is inside of the body during use and the end at which at least one articulated member is located, where this feature is further described infra. As mentioned above, the proximal and distal ends are separated by a distance sufficient to provide for the proximal end to be outside of the body and the distal end to be inside of the body during use, where this distance will vary depending on the particular application in which the device is to be used, e.g., whether the device is to be used in a laparoscopic procedure, to manipulate an object at a vascular site, etc. As such, the distance between the proximal and distal ends in many embodiments of the subject invention generally ranges from about 3 to 60, usually from about 10 to 50 and more usually from about 12 to 50 inches. Depending on the particular application for which the device is intended to be employed, the elongate member may be rigid or flexible. Where the elongate member is rigid, e.g., as would be found in a device designed for use in laparoscopic or other trocar sleeve accessed surgical procedures, the distance between the proximal and distal ends typically ranges from about 3 to 20, usually from 12 to 18 and more usually from about 12 to 15 inches. In those embodiments where the elongate member is flexible, i.e., in "catheter" embodiments of the subject invention where the device is to be used to manipulate an object positioned at a vascular site or another site that is accessed through an analogous tortuous or at least curvilinear pathway, the distance between the proximal and distal ends typically ranges from about 3 to 60, usually from about 10 to 50 and more usually from about 20 to 50 inches.

Located at the distal end of the device is at least one articulated member. In many embodiments, the device includes a plurality of articulated members. By plurality is meant at least 2, where the number may range from 2 to 6, usually 2 to 4 and more usually 2 to 3. In certain embodiments, the device includes a single articulated member. However, in many other embodiments, the device includes two articulated members.

The number of joints in the finger may vary, but typically ranges from about 1 to 10, usually from about 2 to 4 and more usually from about 2 to 3. The length of each finger may vary depending on the particular configuration of the device, e.g. laparoscopic or catheter, but generally ranges from about 0.25 inch to 6 inches, usually from about 0.5 inch to 4 inches and more usually from about 1 to 4 inches. The size of the fingers and elements from which they are made necessarily varies with respect to the size of the object that they are intended to manipulate. For small scale object, i.e., objects having a volume ranging from about 0.01 to 0.25 cubic inches, usually from about 0.02 to 0.20 cubic inches and more usually from about 0.05 to 0.125 cubic inches, such as structures found in vascular locations, food objects in lungs, gall stones, etc., the length of each finger is typically at least about 0.25, usually at least about 0.3 and more usually at least about 0.5 inches, where the length may be as long as 4 inches or longer, but generally does not exceed about 3 and usually does not exceed about 2 inches. For large objects, i.e., objects having a volume ranging from about 27 to 125 cubic inches and usually from about 40 to 100 cubic inches, e.g., tissues, organs, etc., the length of each finger is typically at least about 2, usually at least about 2.5 and more usually at least about 3.0 inches, where the length may be as long as 6 inches or longer, but generally does not exceed about 5 and usually does not exceed about 4 inches. In those embodiments where the device includes a plurality (i.e. two or more) of articulated members (i.e. jointed fingers), all of the members may be of the same length or they may have different lengths, where when the members are of different length, the magnitude of the difference in lengths typically ranges from about 0.5 to 3.0 inches, usually from about 1.0 to 2.0 inches. In many embodiments, all of the articulated members are of the same length. The hinges located at the joints of the finger elements may vary in configuration, where hinge configurations of interest include: torsional springs, compression joints, living hinges, and the like.

The articulated member(s) may have a number of distinct configurations. A feature of the subject devices is that the articulated member(s) is characterized by having at least one of the following two features: (1) the presence of compression means for preventing hyperextension of the member; and (2) the absence of pinned hinges at the joints. In certain embodiments, the articulated member of the device is one that has both of the above features, i.e. one that includes a hyperextension prevention compression means and lacks pinned hinges at its joints. In yet other embodiments, the articulated member includes only one of the above features, i.e. it is one that has pinned hinges at its joints but also includes a compression means for preventing hyperextension or it is one that lacks pinned hinges at its joints and does not have a compression means for preventing hyperextension.

By compression means for preventing hyperextension is meant a means that acts through compression, i.e. through two elements or masses pushing into and against each other, to prevent hyperextension of the member. By hyperextension is meant a movement of the member beyond the extended state in a direction opposite the flexed state. More specifically, like human fingers the articulated members of the subject invention are capable of moving between two states: (1) an extended state in which the member is straight out or extended; and (2) a flexed state in which the member is curled around itself to some extent. The hyper-extended state would be one in which the member was bent around itself to a certain extent in a direction opposite the flexed state. In terms of the analogy to a human finger, the hyper-extended state of a human finger would be one in which the finger was bent backwards away from the palm of the hand and towards the back of the hand and beyond the fully extended finger state. In the compression means of preventing hyperextension of the subject devices, two bodies are pressed together in the extended state of the member and are configured such that, when pressed together, they prevent hyperextension of the finger. Any convenient compression means for preventing hyperextension may be employed, where representative means are described infra.

As mentioned above, certain embodiments of the subject devices are characterized by having joints that are not pinned hinge joints. By pinned hinge joint is meant a joint in which a pin or analogous structure is passed through a hole present at the intersection of two longitudinal elements of the member or finger that holds the two longitudinal elements together in a manner such that they can pivot about each other. As the joints of the articulated members or fingers are ones that are not pinned hinges, they have a configuration that provides for the requisite pivot movement without a pinned hinge, where representative non-pinned hinge joints are described in greater detail infra, e.g., FIGS. 1 to 7 and 10, and the description thereof.

In certain embodiments where the device includes a plurality of articulated members, i.e. two or more articulated members, each articulated member of the device is capable of being moved independently relative to the other articulate member(s) of the device. In other words, one articulated member can be moved without moving the other articulated member or members of the device. While these embodiments in which the articulated members are independently movable may or may not include one or both of the above features, i.e. the presence of a compression means for preventing hyperextension or the absence of joints with pinned hinges, in many of the devices of this embodiment at least one of these features is present.

The direction that the articulate member(s) flexes in the subject devices may vary depending on the intended use of the subject device. For example, in certain embodiments the articulated member may flex towards the longitudinal axis of the device with which it is associated, e.g., towards the longitudinal of the tubular portion of the device from which it protrudes at the distal end. This configuration is found generally in grasper embodiments of the subject invention where the subject device is employed to grab hold of or grasp an object, e.g., tissue, organ etc. In yet other embodiments, the articulated member may flex away from the longitudinal axis of the device with which it is associated, e.g., away from the longitudinal axis of the tubular portion of the device from which it protrudes at the distal end. This configuration is found generally in spreader embodiments of the subject invention where the subject device is employed to separate or spread objects, e.g., organs or tissues.

In certain embodiments of the subject devices, the articulated member or members are capable of being retracted into and protruded from a protective housing located at the distal end of the elongate, e.g. tubular device. In many embodiments, the distal and proximal ends are separated by an elongate tubular region that may be flexible or rigid, depending on the configuration of the device, as described supra. In these embodiments, the protective housing is simply the opening of the tube at the distal end through which the articulate members may be extended or retracted. As such, during introduction of the distal end of the device that includes the articulated members into the body during use, the articulated members or fingers may be retracted into the protective housing to aid in placement of the device at the location of the internal object to be manipulated. After the distal end of the device has been positioned at the location of the object to be manipulated, the fingers may be protruded from the protective housing.

As mentioned above, the distal and proximal ends are generally separated by an elongated tubular member. While in many embodiments the cross-sectional shape of the member is curvilinear and most typically circular, other cross-sectional shapes are possible, e.g. square, rectangular, trapezoidal, triangular etc. The longest cross sectional dimension of the tubular elongate portion of the device may vary depending on the configuration of the device, but typically ranges from about 0.1 to 2.5, usually from about 0.3 to 2.0 and more usually from about 0.4 to 1.5 cm. In those embodiments of the device where the elongate member is rigid, the longest cross-sectional dimension of the elongate portion, e.g. the diameter of the tubular section, typically is at least about 0.1 cm, usually at least about 0.3 cm and more usually at least about 0.4 cm, where the longest cross-sectional dimension may be as long as 2.5 cm or longer, but generally does not exceed about 2.0 cm and usually does not exceed about 1.5 cm. In those embodiments of the device where the elongate member is flexible, e.g. in the "catheter" embodiments of the subject devices, the longest cross-sectional dimension of the elongate portion, e.g. the diameter of the tubular section, typically is at least about 0.1 cm, usually at least about 0.15 cm and more usually at least about 0.2 cm, where the longest cross-sectional dimension may be as long as 2.0 cm or longer, but generally does not exceed about 1.0 cm and usually does not exceed about 0.75 cm.

In certain embodiments, the device further comprises an articulated member locking means, which serves to lock the articulated members in a given position, e.g., in a gripped position, in an open position etc.

Located at the proximal end of the device is a manual actuation means for moving the distal articulated members between a first extended position and a second flexed position. In other words, a manual means is positioned at the proximal end of the device for actuating the articulate members to assume various configurations, e.g., extended, grasped, semi-grasped, etc. The manual actuation means may be present in a variety of different configurations, so long as it is capable of providing for the requisite manual control over the movement of the articulate fingers during use of the device. As such, any manual actuation means that can be operated by hand from a site external to the body and achieve the desired internal object manipulation or movement via the internal articulated member(s) during use may be present on the device. The manual actuation means typically includes one or more elements shaped or configured to be operated by fingers and/or a thumb which are operationally connected to the articulated members via wires, strings, cables, or other tensile elements, etc., to provide for the desired articulate member movement. Manual actuation means of interest include adaptations of those described in U.S. Patents of interest include: U.S. Pat. Nos. 5,997,567; 5,976,122; 5,891,162; 5,820,009; 5,797,959; 5,728,121; 5,713,919; 5,613,973; 5,549,636; 5,417,684; and 5,383,895; the disclosures of which are herein incorporated by reference. Representative manual actuation means are described infra in greater detail.

As mentioned above, many embodiments of the subject devices include a means for moving the articulated members from a retracted to a deployed position, where the retracted position is used during introduction of the device into the body and the deployed position is used during manipulation of the internal body object with the device. In many of these embodiments, the device further includes at the proximal end a locking means for reversibly locking the articulated members in the deployed position. Any convenient locking means may be employed, where a representative locking means is described further in terms of the figures, infra.

The individual elements of the subject devices may be fabricated from any convenient material, where at least the distal portion of the device and elements present at the distal portion, e.g., the articulated members, the elongate member, etc., are ones that are fabricated from a biocompatible material. Bicompatible materials of interest include biocompatible polymers, where suitable biocompatible polymers include, but are not necessarily limited to: biocompatible polymers and/or elastomers. Suitable biocompatible polymers include, but are not necessarily limited to, materials such as, for example, polyethylene, homopolymers and copolymers of vinyl acetate such as ethylene vinyl acetate copolymer, polyvinylchlorides, homopolymers and copolymers of acrylates such as polypropylene, polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as polytetrafluoroethylene and polyvinyl fluoride, polystyrenes, homopolymers and copolymers of styrene acrylonitrile, cellulose acetate, homopolymers and copolymers of acrylonitrile butadiene styrene, polyvinylchloride, silicone rubber, polymethylpentene, polysulfones, polyesters, polyimides, polyisobutylene, polymethylstyrene and other similar compounds known to those skilled in the art. Suitable, biocompatible elastomers include, but are not necessarily limited to, biocompatible elastomers such as medical grade silicone rubbers, polyvinyl chloride elastomers, polyolefin homopolymeric and copolymeric elastomers, urethane-based elastomers, and natural rubber or other synthetic rubbers, fluorenated polymers (e.g., PTFE), and the like. In the catheter versions of the subject devices, the material from which the device is fabricated may include a radiodense material or some other imaging means to allow for visualization, e.g., with fluoroscopy. It should be understood that these possible biocompatible materials are included above for exemplary purposes and should not be construed as limiting.

In certain embodiments, the subject devices include a shape memory element or elements. Any convenient shape memory material which provides for the requisite features of flexibility and resumption of configuration following removal of applied force may be employed in these embodiments. As such, shape memory alloys find use. A variety of shape memory alloys are known, including those described in: U.S. Pat. Nos. 5,876,434; 5,797,920; 5,782,896; 5,763,979; 5,562,641; 5,459,544; 5,415,660; 5,092,781; 4,984,581; the disclosures of which are herein incorporated by reference. The shape memory alloy that is employed should generally be a biocompatible alloy. Specific biocompatible alloys that find use include those nickle-titanium (NiTi) shape memory alloys sold under the Nitinol™ name by Memry Corporation (Brookfield, Conn.); spring steel, etc. Also of interest are shape memory polymeric or plastic materials, where such materials include polypropylene, polyethylene, etc.

The subject devices may be manufactured using any convenient protocol, where suitable protocols are known in the art. Representative manufacturing methods that may be employed include machining, extrusion, and the like.

Figure 1:
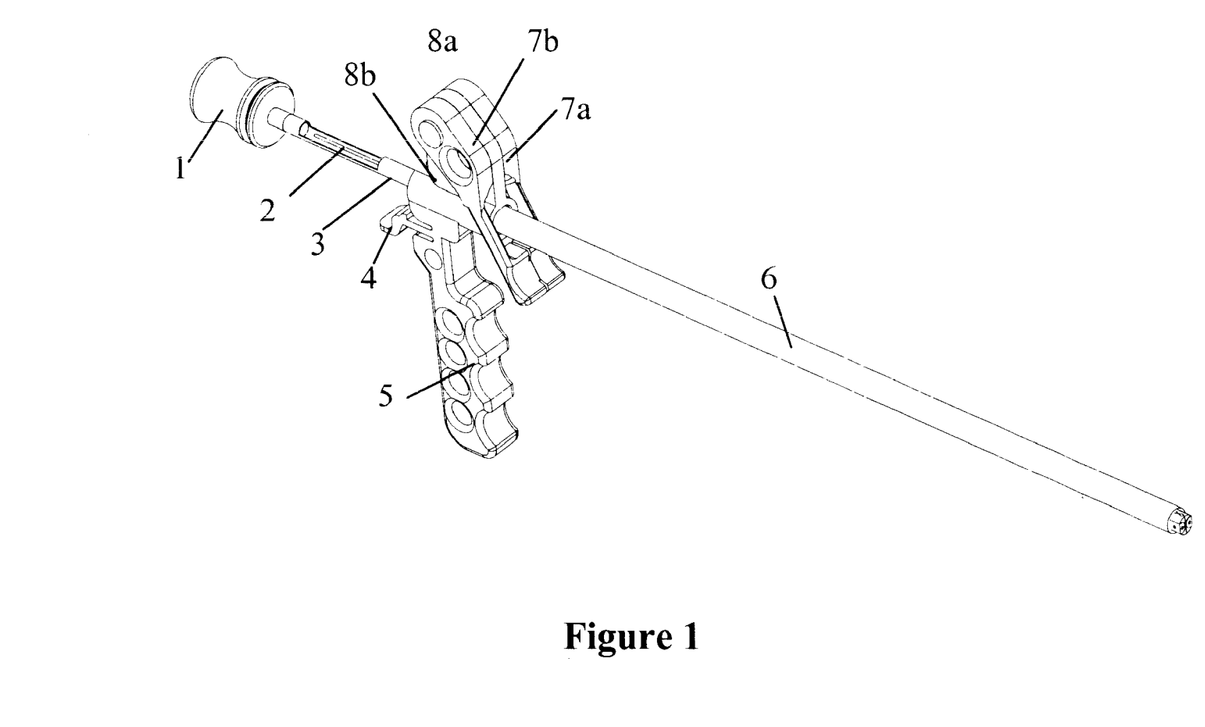
FIG. 1 provides a three-dimensional view of a first embodiment of the subject devices in which the elongate member is rigid, where the device is depicted in a first, retracted position.

Turning now to the figures, FIG. 1 provides a three-dimensional view of a first embodiment of the subject devices in which the elongate member is rigid, where the device is depicted in a first, retracted position. The device shown in FIG. 1 has rigid elongate member 6. At the distal end of the elongate member 6 are the retracted articulated members. At the proximal end of elongate member 6 is the manual operation means. The manual operation means is made up of handle 5, locking means 4, triggers 7a and 7b, retractor/rotator element 1, connector 3 (which serves to structure connect the retractor/rotator 1 to the articulate members at the distal end such that when the retractor/rotator is moved, the articulated members move in the same fashion), tensile element 2 and pins 8a and 8b (for independently moving the articulated members with the triggers). Retractor/rotator element 1 provides for retraction and deployment of the fingers at the distal end of the device, as well as rotation of the fingers at the distal end of the device.

Figure 2:
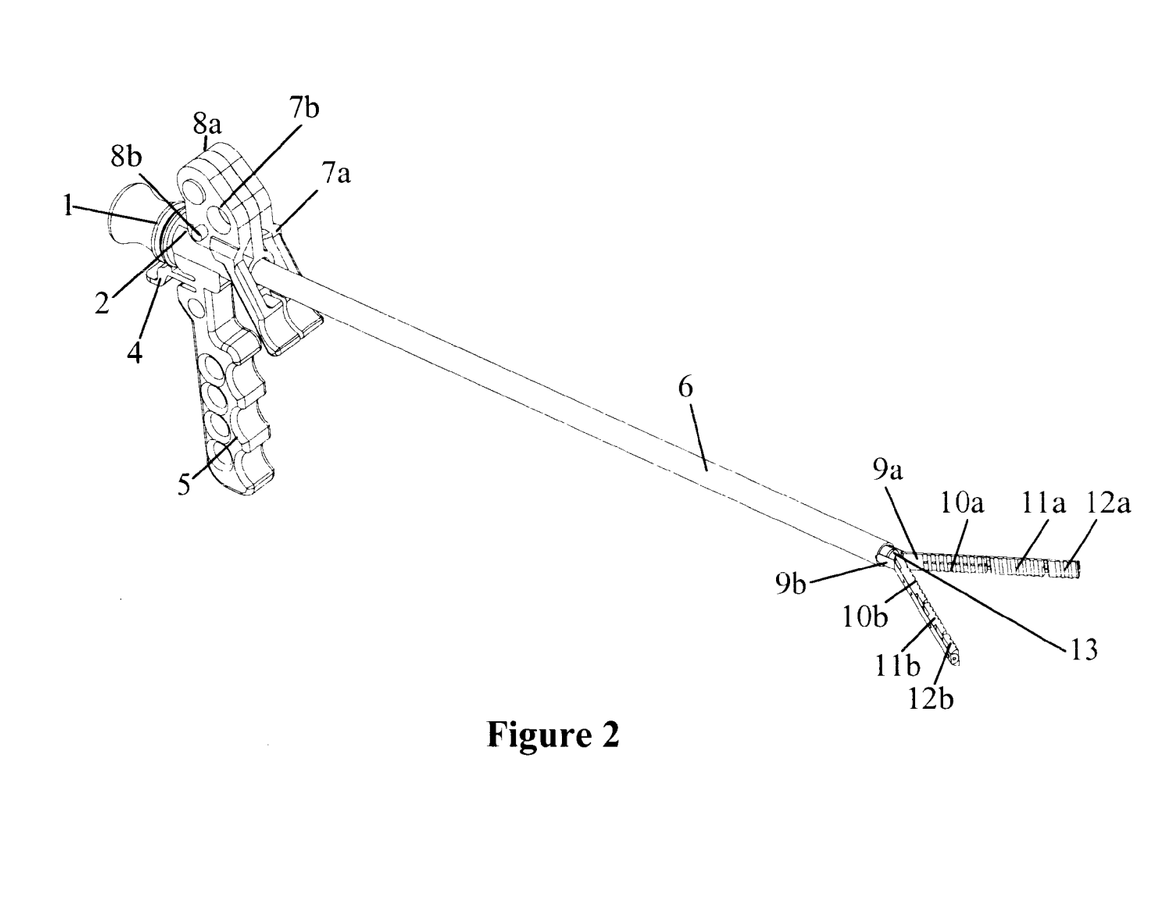
FIG. 2 provides a three-dimensional view of the device shown in FIG. 1, where the device is depicted in the deployed position with fingers extended.

FIG. 2 provides a three-dimensional view of the device shown in FIG. 1, where the device is depicted in the deployed position. Retractor/rotator element 1 is pushed forward and locked into position by locking means 4, thereby moving the articulated members out of the elongate member 6 into the deployed position. This element can be rotated to provide for analogous rotation of the deployed finger elements. The articulated members or fingers are joined at element 13. As shown in FIG. 2, each articulated member is made up of 3 finger elements (10a, 11a and 12a or 10b, 11b and 12b) where each finger is backed by shape memory element (9a or 9b) that runs the length of the finger.

Figure 3:
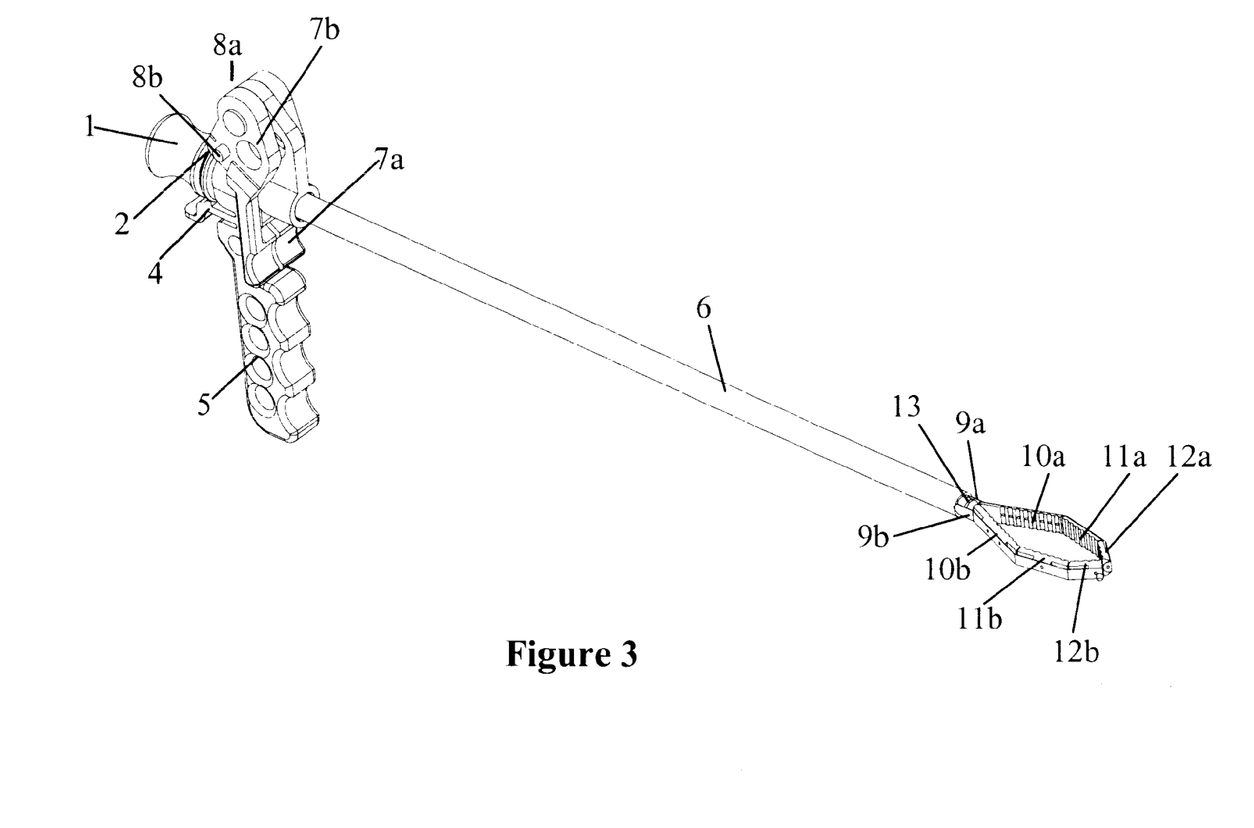
FIG. 3 provides a three-dimensional view of the device shown in FIG. 1, where the device is depicted in the flexed or engaged position.

FIG. 3 provides a three-dimensional view of the device shown in FIG. 1, where the device is depicted in the gripped position. To achieve the gripped position, triggers 7a and 7b are pulled back toward handle 5 as shown in FIG. 3. This movement causes elements 8a and 8b to pull back on tensile element 2, which in turn causes the finger elements to grip inward in a direction opposite the force of the shape memory backing.

Figure 4:
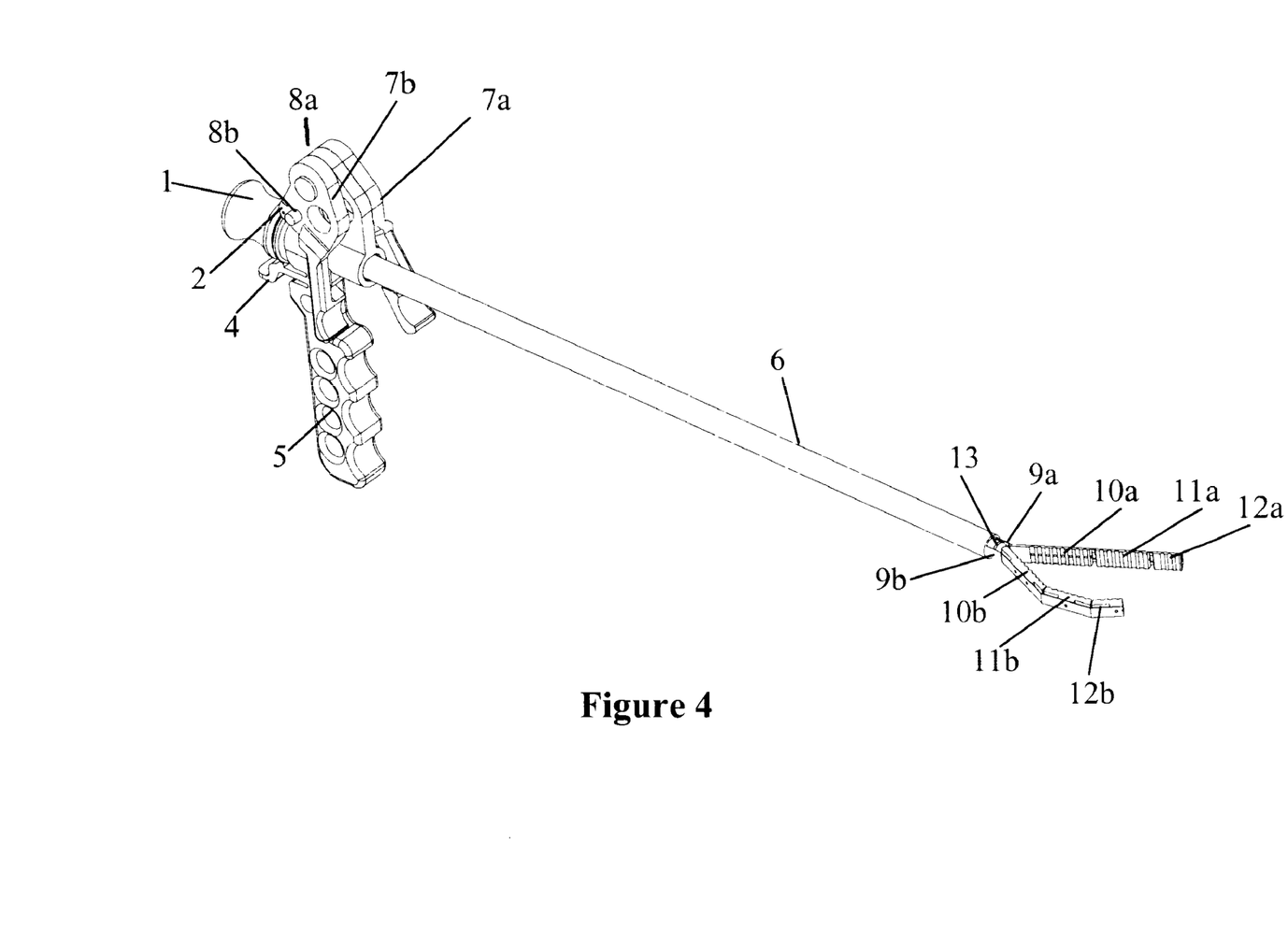
FIG. 4 provides a three-dimensional view of the device shown in FIG. 1, where the device is depicted with one finger flexed or engaged, i.e., in a one-finger flexed position. This figure shows the ability of the articulated members or figures to move independently of each other.

FIG. 4 provides a three-dimensional view of the device shown in FIG. 1, where the device is depicted with one finger flexed and the other finger extended. To achieve this position, only trigger 7b is pulled back while trigger 7a is not. This figure demonstrates that the articulated members are independently actuatable.

Figure 5:
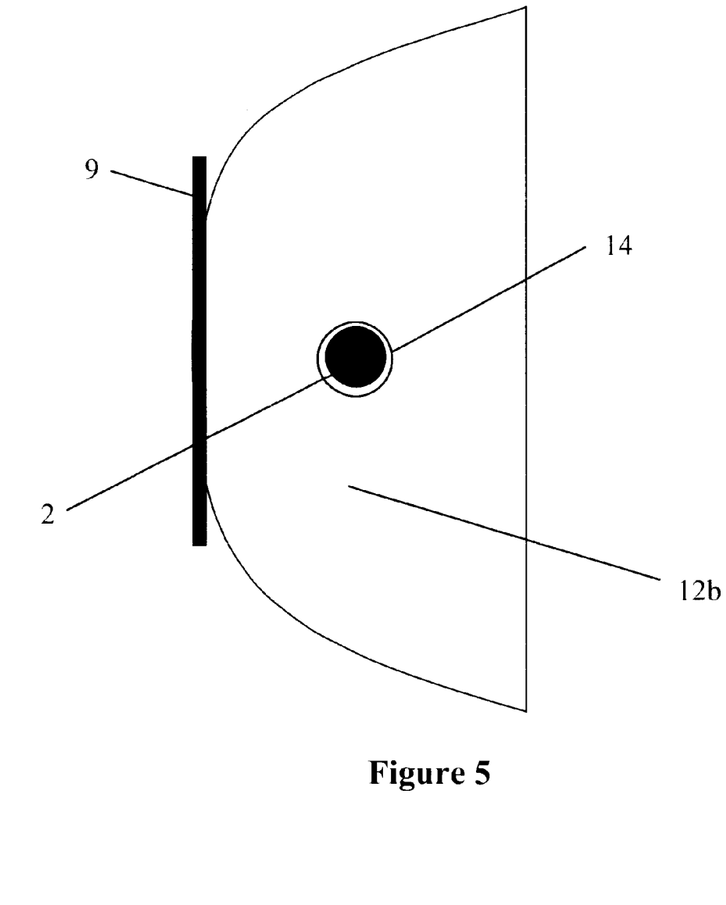
FIG. 5 provides a cross-sectional view of a spring steel (or analogous material) backed finger grasper segment found in certain embodiments of the subject devices.

FIG. 5 provides a cross-sectional view of a spring steel backed finger grasper segment found in certain embodiments of the subject devices. As shown in FIG. 5, when tensile element 2 is pulled, it causes a moment resisted by the spring backing 9. As the moment created by tensile element 2 increases, the finger segment rotates and creates the grasping motion.

Figure 6:
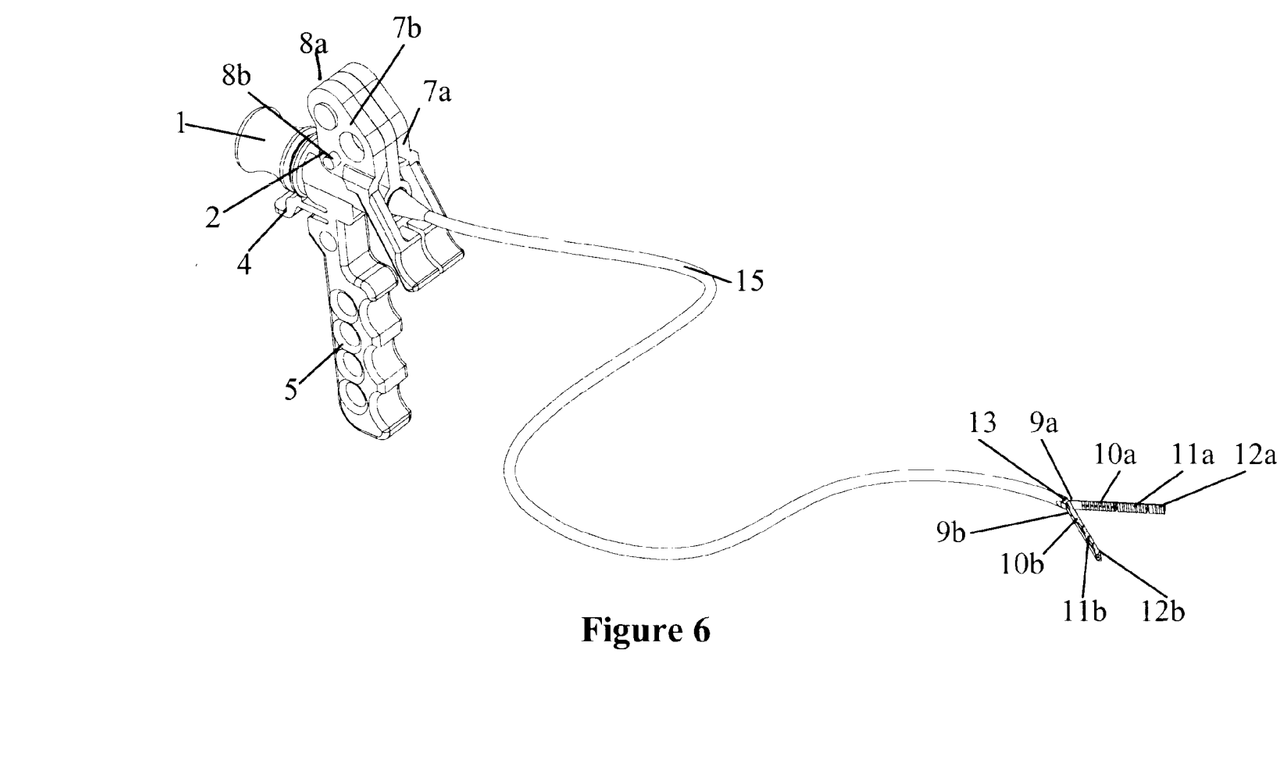
FIG. 6 provides a three-dimensional view of device according to another embodiment of the subject invention in which the elongate member is flexible. In this depiction, the articulated members are portrayed in the extended position.

FIG. 6 provides a three-dimensional view of device according to another embodiment of the subject invention in which the elongate member 15 is flexible. In this depiction, the articulated members are portrayed in the extended position.

Figure 7:
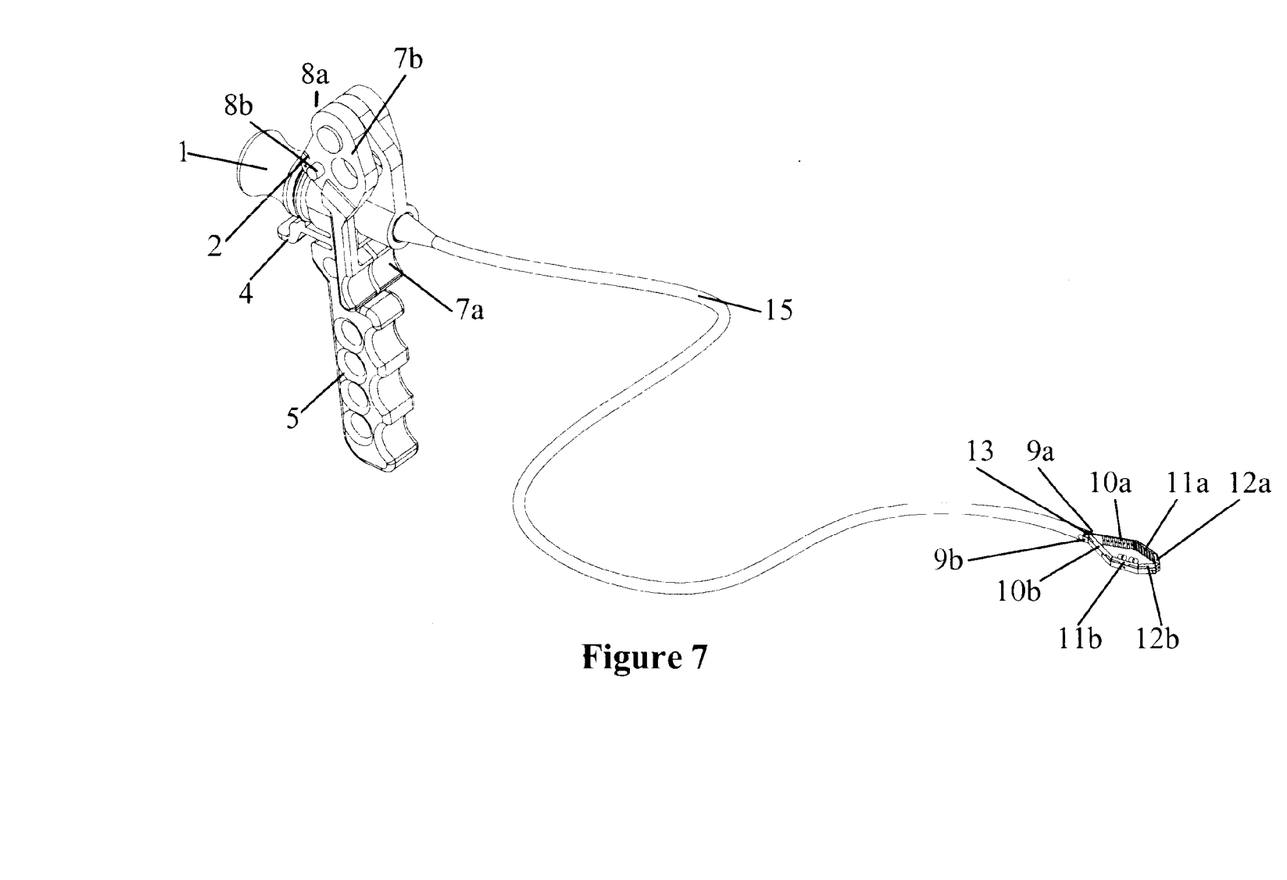
FIG. 7 provides another three-dimensional view of the device shown in FIG. 6, wherein the articulated members are depicted in the flexed position.

FIG. 7 provides another three-dimensional view of the device shown in FIG. 6, wherein the articulated members are depicted in the grasped position.

Figure 8A:
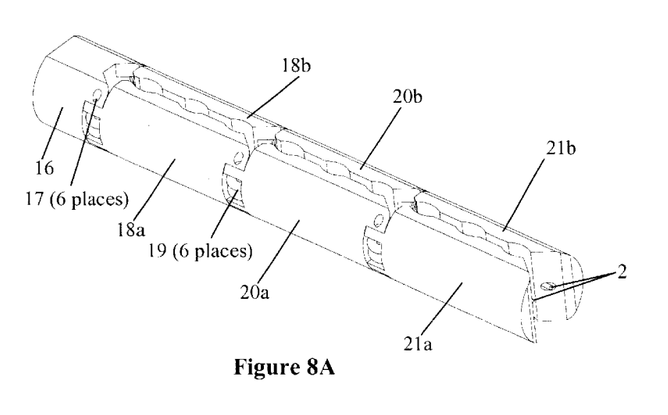
FIGS. 8A to 8C provide a depiction of another embodiment of the articulated members, in which the segments are connected by joints which have torsion springs.
Figure 8B:
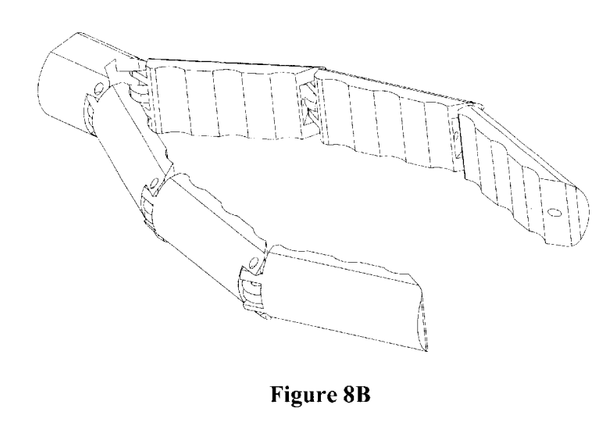
Figure 8C:
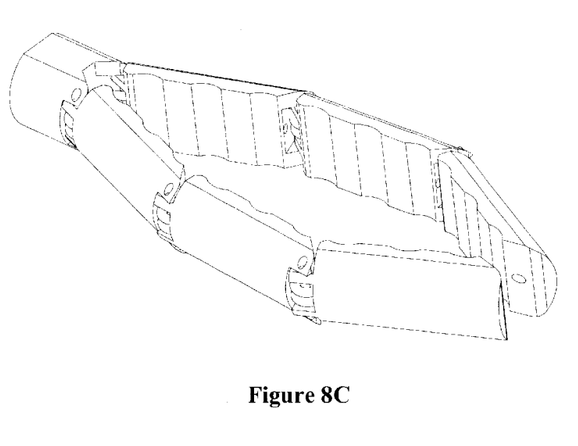

FIGS. 8A to 8C provide a depiction of a close up view of articulated members in which the segments are joined by pinned hinges and the return force is provided by the torsion springs. In FIG. 8A, the fingers are shown in the retracted position. The fingers are joined at element 16. The fingers are made up of three jointed members, i.e., 18a, 20a and 21a or 18b, 20b and 21b. Between each jointed member and the joint 16 is torsion spring joint, shown in the figure as 17 and 19. FIG. 8B shows the same articulated member configuration in the semi-flexed or semi gripped position while FIG. 8C shows the same articulated member configuration in the fully flexed or gripped configuration. Also shown in these figures is string or cable element 2.

Figure 9A:
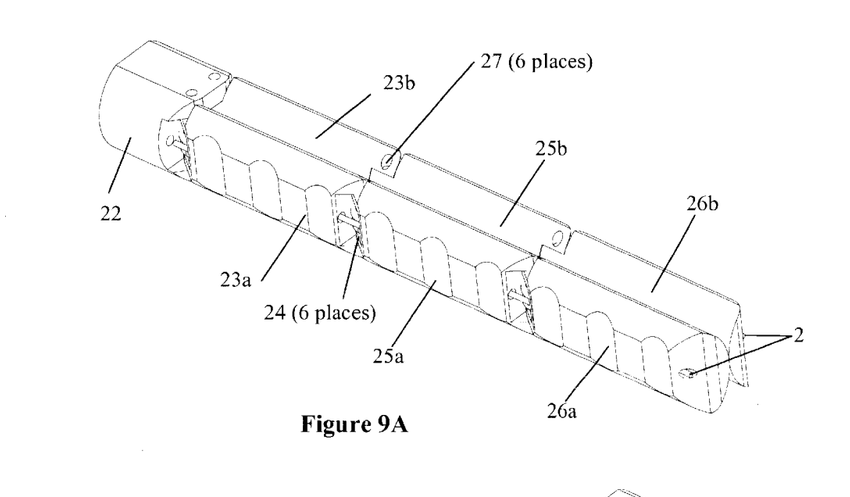
FIGS. 9A to 9B provide a representation of the articulated members of a spreader device, in which the individual finger segments are connected by joints which have torsion springs, analogous to those depicted in the grasper device of FIG. 8.
Figure 9B:
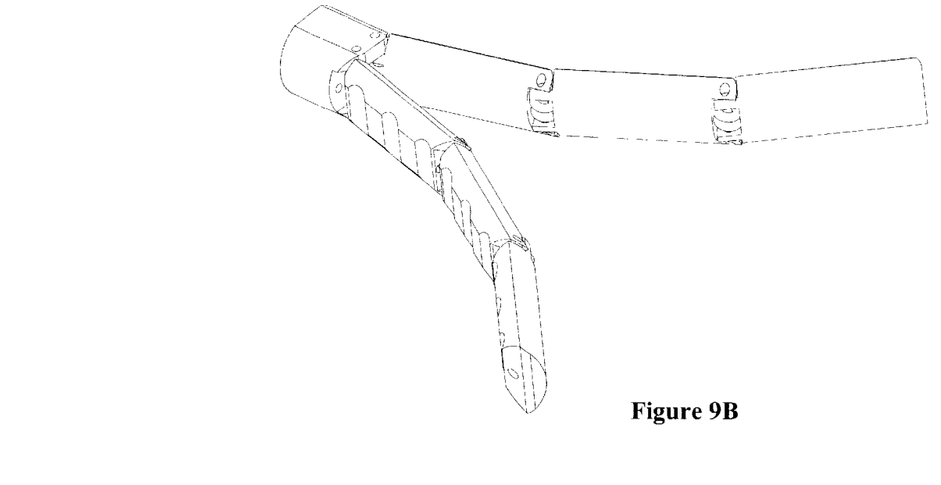

FIGS. 9A to 9B provide a representation of the articulated members of a spreader device, in which the individual finger segments are joined by pinned hinges and the return force is provide by the torsion springs, analogous to those depicted in the grasper device of FIG. 8. FIG. 9A shows the device in the retracted position and FIG. 9B shows the device in the deployed, flexed spread position.

Figure 10A:
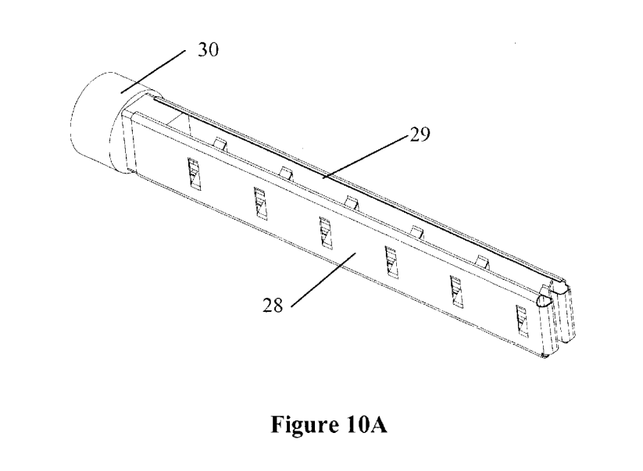
FIG. 10A to 10C provides a three-dimensional view of a "memory-metal" embodiment of the articulate members of the subject devices.
Figure 10B:
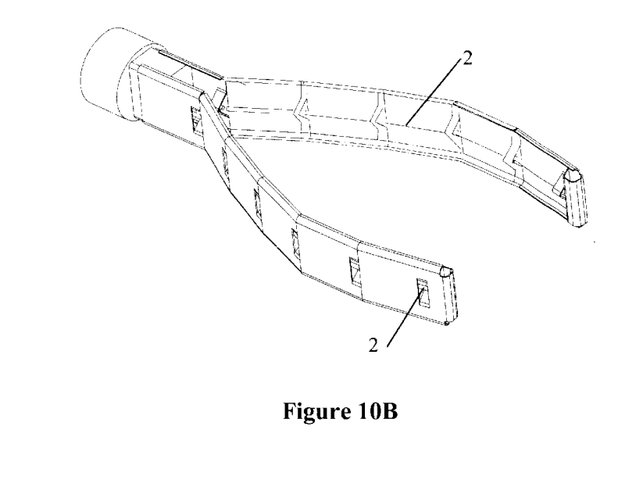
Figure 10C:
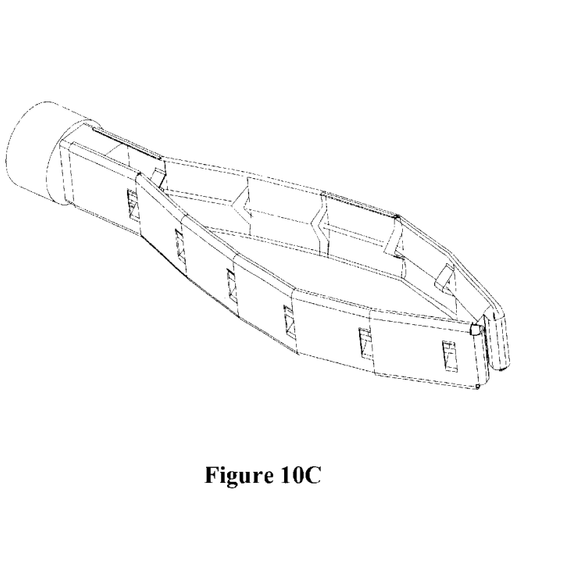

FIG. 10A to 10C provides a three-dimensional view of a "memory-metal" embodiment of the articulate members of the subject devices. In this embodiment, each finger is made up of a strip of memory metal which assumes the configuration of FIG. 10B when deployed. Pulling of element 2 produces the gripped configuration as shown in FIG. 10C.

UTILITY

The subject devices find use in methods in which an internal object inside an animal is manipulated from a site external to the animal. As such, the subject devices are suited for use in minimally invasive or "non-open" surgical procedures in which an internal body object is manipulated from a location outside of the animal. By manipulated from a site or location outside of the animal is meant that the surgeon or analogous health care professional's hands are present at a site outside of the animal and, via the device, remotely manipulate tissue inside the animal.

The subject devices may be used to remotely manipulate internal body objects in a variety of different manners depending on the particular design of the device being employed. For example, in certain embodiments the devices may be employed to grasp or hold internal body objects. In yet other embodiments, the subject devices may be employed to separate or spread internal body objects from each other.

A variety of different types of internal body objects may be manipulated using the subject devices and methods. The term "internal body object" is used broadly to refer to any type of object or structure that is inside the animal body, i.e., not on the surface or epidermis of the animal. Representative structures that may be manipulated employing the subject devices in the subject methods include: tissues, organs or parts thereof, internal vascular objects, e.g., vascular obstructions or lesions, food particles and other foreign body objects, and the like.

The subject methods and devices find use with a variety of different types of animals. Representative animals with which the subject methods and devices find use include, but are not limited to: canines; felines; equines; bovines; ovines; etc. and primates, particularly humans.

KITS

Also provided are kits that at least include the subject devices. The subject kits at least include a device of the subject invention and instructions for how to use the device in a procedure. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g. CD-ROM, diskette, etc. The instructions may take any form, including complete instructions for how to use the device or as a website address with which instructions posted on the world wide web may be accessed.

The following examples are offered by way of illustration and not by way of limitation.

EXPERIMENTAL

I. Use of the Device

A. Laparoscopic application:

The device shown in FIG. 1 is inserted through the appropriately sized trocar sleeve into the abdominal cavity. Next, the fingers are advanced through the sheath. Following advancement through the sheath, the fingers spring into their preferred, deployed shape. This preferred shape is one in which the fingers are positioned away from each other. At this point, the rotator/retractor knob (element 1 as shown in FIG. 1) on the proximal end is locked into position by locking element 4, locking the inner cylinder(connector 3)/fingers in relation to the outer sheath. Now, the proximal handle is manipulated through flexion of the operator's fingers to cause flexion of the fingers located on the distal end of the device. This flexion of the distal fingers of the device allows grasping of various sized objects, including, but not limited to, the gall bladder, gall stones, colon, spleen, kidney, adrenals glands, stomach, and pancreas.

Other non-laparoscopic applications in which the grasping device depicted in FIG. 1 finds use include, but are not limited to, orthopedic applications (including arthroscopy), urologic applications, cardiothoracic applications (including on and off pump cardiac operations), and obstetric/gynecologic applications. The use of a trocar sleeve to facilitate entry/exit of the device may or may not be required.

B. Catheter application (Retrieval of foreign body in lung)

In this case, the catheter based version of the device as shown in FIGS. 6 and 7 is used as follows. In the case of retrieval of a foreign body from the lungs, a rigid or flexible bronchoscope is advanced thorough the pulmonary tree (trachea, bronchus, bronchioloes) until the foreign body (e.g. a food item) is located. At this point, the catheter is advanced through the lumen of the bronchoscope, and under bronchoscopic visualization, the foreign body is grasped by the distal aspect of the device. Next, the bronchoscope and catheter device are removed together, pulling out the foreign body as the devices are themselves removed.

Alternative catheter-based applications include but are not limited to interventional cardiology, interventional radiology, and neurointerventional radiology. Applications may include retrieval of foreign objects or other objects such as thrombus or emboli. Other applications also include gastroenterology which might involve retrieval of foreign objects within the alimentary tract using fluoroscopic or endoscopic guidance.

It is evident that the subject devices provide for a number of important advantages over prior art minimally invasive surgical tools. The subject devices show great dexterity in that one can grasp and shift internal objects easily by individually flexing the articulated members and rotating the members. Furthermore, the subject devices are able to curve around and grab an object without applying excessive or damaging force to the object, much like a human finger. In other words, the subject devices may be used to manipulate both small and large objects with great dexterity in an atraumatic way. Furthermore, certain embodiments of the device provide the ability to grasp large objects. The subject devices are also easy to master and use, and are applicable to a large number of different applications. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A surgical device comprising:
   proximal and distal ends;
   at least one articulated member comprising a shape memory element located at said distal end, wherein said articulated member comprises compression means for preventing hyperextension of said member and joints that are not pinned hinge joints; and
   a manual actuation means located at said proximal end for actuating said at least one articulated member.

2. The surgical device according to claim 1, wherein said device comprises a plurality of articulated members.

3. The surgical device according to claim 2, wherein said device comprises two articulated members.

4. The surgical device according to claim 2, wherein said articulated member of said plurality is individually actuatable relative to any other articulated member of said plurality.

5. The surgical device according to claim 1, wherein said device comprises a rigid elongate member separating said proximal and distal ends.

6. The surgical device according to claim 1, wherein said device comprises a flexible elongate member separating said proximal and distal ends.

7. The surgical device according to claim 1, wherein said at least one articulated member is retractable into a protective housing located at said distal end.

8. A surgical device comprising:
   proximal and distal ends separated by an elongate member;
   at least one articulated member comprising a shape memory element located at said distal end, wherein said articulated member comprises joints that are not pinned hinge joints; and
   a manual actuation means located at said proximal end for actuating said at least one articulated member.

9. The surgical device according to claim 8, wherein said device comprises a plurality of members.

10. The surgical device according to claim 9, wherein said device comprises two articulated members.

11. The surgical device according to claim 9 wherein said articulated member of said plurality is individually actuatable relative to any other articulated member of said plurality.

12. The surgical device according to claim 8, wherein said device comprises a rigid elongate member separating said proximal and distal ends.

13. The surgical device according to claim 8, wherein said device comprises a flexible elongate member separating said proximal and distal ends.

14. The surgical device according to claim 8, wherein said at least one articulated member is retractable into a protective housing located at said distal end.

15. The surgical device according to claim 8, wherein said at least one articulated member comprises compression means for preventing hyperextension of said member.

16. A surgical device comprising:
   proximal and distal ends;
   a plurality of articulated members located at said distal end, wherein each articulated member of said plurality comprises a shape memory element and is individually actuatable relative to any other articulated member of said plurality and comprises joints that are not pinned hinge joints; and
   a manual actuation means located at said proximal end for independently actuating each articulated member of said plurality.

17. The surgical device according to claim 16, wherein said device comprises two articulated members.

18. The surgical device according to claim 16, wherein said device comprises a rigid elongate member separating said proximal and distal ends.

19. The surgical device according to claim 16, wherein said device comprises a flexible elongate member separating said proximal and distal ends.

20. The surgical device according to claim 16, wherein said plurality is retractable into a protective housing located at said distal end.

21. The surgical device according to claim 16, wherein each articulated member of said plurality comprises compression means for preventing hyperextension of said member.

22. A method for manipulating an object inside a body, said method comprising:
   introducing the distal end of a surgical device comprising at least one articulated member according to claims 1, 9 or 17 into said body; and
   manipulating said object with said at least one articulated member;
   whereby said object is manipulated inside said body.

23. The method according to claim 22, wherein said device comprises a rigid elongate member separating said proximal and distal ends.

24. The method according to claim 22, wherein said device comprises a flexible elongate member separating said proximal and distal ends.

25. A kit for use in a method according to claim 22, said kit comprising:
   a surgical device according to claims 1, 8 or 16; and
   instructions for using said device.

* * * * *

UNITED STATES PATENT AND TRADEMARK OFFICE
CERTIFICATE OF CORRECTION

PATENT NO.    : 6,443,944 B1
DATED         : September 3, 2002
INVENTOR(S)   : Doshi, Rajiv et al.

It is certified that error appears in the above-identified patent and that said Letters Patent is hereby corrected as shown below:

<u>Column 13,</u>
Line 9, please replace "9 or 17 into said body; and" with -- 8 or 16 into said body; and --

Signed and Sealed this

Tenth Day of December, 2002

JAMES E. ROGAN
*Director of the United States Patent and Trademark Office*